US010672511B2

(12) United States Patent
Patrick

(10) Patent No.: US 10,672,511 B2
(45) Date of Patent: Jun. 2, 2020

(54) FRAMEWORKS AND METHODOLOGIES CONFIGURED TO ENABLE DESIGN AND IMPLEMENTATION OF CUSTOMISED CLINICAL INFORMATION SYSTEMS, ENABLE NATIVE INTEROPERABILITY BETWEEN CUSTOMISABLE CLINICAL INFORMATION SYSTEMS, ENABLE PROCESS EFFICIENCY MANAGEMENT IN CLINICAL INFORMATION SYSTEMS

(71) Applicant: INNOVATIVE CLINICAL INFORMATION MANAGEMENT SYSTEMS PTY LTD (ICIMS), Eveleigh, New South Wales (AU)

(72) Inventor: Jon Patrick, Sydney (AU)

(73) Assignee: Innovative Clinical information Management Systems Pty Ltd (iCIMS), Eveleigh (AU)

( * ) Notice: Subject to any disclaimer, the term of this patent is extended or adjusted under 35 U.S.C. 154(b) by 548 days.

(21) Appl. No.: 15/319,363

(22) PCT Filed: Jun. 16, 2015

(86) PCT No.: PCT/AU2015/000352
§ 371 (c)(1),
(2) Date: Dec. 15, 2016

(87) PCT Pub. No.: WO2015/192165
PCT Pub. Date: Dec. 23, 2015

(65) Prior Publication Data
US 2017/0124265 A1 May 4, 2017

(30) Foreign Application Priority Data

Jun. 16, 2014 (AU) ................................ 2014902286
Jun. 16, 2014 (AU) ................................ 2014902288

(Continued)

(51) Int. Cl.
*G06F 21/62* (2013.01)
*G16H 40/20* (2018.01)
(Continued)

(52) U.S. Cl.
CPC .......... *G16H 40/20* (2018.01); *G06F 21/6245* (2013.01); *G06Q 50/24* (2013.01); *G06Q 10/00* (2013.01)

(58) Field of Classification Search
CPC ........ G16H 10/60; G16H 40/20; G16H 50/20; G16H 10/40; H04L 67/02; H04L 63/20;
(Continued)

(56) References Cited

U.S. PATENT DOCUMENTS 7,286,997 B2 10/2007 Spector et al.
2005/0222873 A1 10/2005 Nephin et al.
(Continued)

OTHER PUBLICATIONS

ISA Australian Patent Office, International Search Report Issued in Application No. PCT/AU2015/000352, dated Sep. 3, 2015, WIPO, 5 pages.
(Continued)

*Primary Examiner* — Maroun P Kanaan
(74) *Attorney, Agent, or Firm* — McCoy Russell LLP

(57) ABSTRACT

Described herein are relates to frameworks and methodologies configured to enable design and implementation of customised clinical information systems. One embodiment includes a computer implemented method for providing Clinical Information System (CIS) functionalities, the framework including: providing a plurality of purpose-specific CIS interfaces, wherein each interface is renderable at a given client terminal based on CIS interface design data, wherein the CIS interface design data includes: (i) content pages, wherein each content page is configured to contain one or more page objects; and (ii) logical rules defining
(Continued)

navigation and behaviour of content pages; providing access to a common central patient information database; providing a content and process design user interface, thereby to enable a user of a client terminal to define, by way of a graphical Interface, CIS interface design data; and operating a content and process engine.

18 Claims, 8 Drawing Sheets

(30) Foreign Application Priority Data

| | | | |
|---|---|---|---|
| Jun. 16, 2014 | (AU) | ................................ | 2014902290 |
| Jun. 16, 2014 | (AU) | ................................ | 2014902294 |
| Jun. 16, 2014 | (AU) | ................................ | 2014902296 |

(51) Int. Cl.
*G06Q 50/24* (2012.01)
*G06Q 10/00* (2012.01)

(58) Field of Classification Search
CPC ..... H04L 67/00; G06F 16/958; G06F 16/904; G06F 16/9024; G06F 19/00; G06F 8/10; G06F 8/24; G06F 8/35; G06F 8/77; G06N 3/08; G06N 5/02; G06N 7/00; G06Q 50/24

See application file for complete search history.

(56) References Cited

U.S. PATENT DOCUMENTS

| | | |
|---|---|---|
| 2007/0168223 A1 | 7/2007 | Fors et al. |
| 2009/0164249 A1 | 6/2009 | Hunt et al. |
| 2010/0070448 A1* | 3/2010 | Omoigui ............. H01L 27/1463 706/47 |
| 2010/0131482 A1 | 5/2010 | Linthicum et al. |

OTHER PUBLICATIONS

ISA Australian Patent Office, Written Opinion of the International Searching Authority Issued in Application No. PCT/AU2015/000352, dated Sep. 3, 2015, WIPO, 12 pages.

* cited by examiner

FRAMEWORKS AND METHODOLOGIES CONFIGURED TO ENABLE DESIGN AND IMPLEMENTATION OF CUSTOMISED CLINICAL INFORMATION SYSTEMS, ENABLE NATIVE INTEROPERABILITY BETWEEN CUSTOMISABLE CLINICAL INFORMATION SYSTEMS, ENABLE PROCESS EFFICIENCY MANAGEMENT IN CLINICAL INFORMATION SYSTEMS

CROSS-REFERENCE TO RELATED APPLICATIONS

The present application is a U.S. National Phase of International Patent Application Serial No. PCT/AU2015/000352, entitled "FRAMEWORKS AND METHODOLOGIES CONFIGURED TO ENABLE DESIGN AND IMPLEMENTATION OF CUSTOMISED CLINICAL INFORMATION SYSTEMS, ENABLE NATIVE INTEROPERABILITY BETWEEN CUSTOMISABLE CLINICAL INFORMATION SYSTEMS, ENABLE PROCESS EFFICIENCY MANAGEMENT IN CLINICAL INFORMATION SYSTEMS AND/OR ENABLE IMPLEMENTATION OF INDEPENDENT FORMAL ONTOLOGY VALUES IN CUSTOMISED CLINICAL INFORMATION SYSTEMS," filed on Jun. 16, 2015. International Patent Application Serial No. PCT/AU2015/000352 claims priority to Australian Patent Application No. 2014902286, filed on Jun. 16, 2014; and to Australian Patent Application No. 2014902288, filed on Jun. 16, 2014; and to Australian Patent Application No. 2014902290, filed on Jun. 16, 2014; and to Australian Patent Application No. 2014902294, filed on Jun. 16, 2014; and to Australian Patent Application No. 2014902296, filed on Jun. 16, 2014. The entire contents of each of the above-cited applications are hereby incorporated by reference for all purposes.

FIELD OF THE INVENTION

The present invention relates to frameworks and methodologies configured to enable design and implementation of customised clinical information systems. Some embodiments have been particularly developed for providing a hybrid between best-of-breed architecture and enterprise architecture, thereby to allow a clinical environment to leverage advantages associated with each. Some embodiments have been developed to enable native interoperability between customisable clinical information systems. Some embodiments have been developed to enable process efficiency management in clinical information systems. Some embodiments have been developed to enable implementation of independent formal ontology values in customised clinical information systems.

While some embodiments will be described herein with particular reference to that application, it will be appreciated that the invention is not limited to such a field of use, and is applicable in broader contexts.

BACKGROUND

Any discussion of the background art throughout the specification should in no way be considered as an admission that such art is widely known or forms part of common general knowledge in the field.

The use of Clinical Information Systems (CIS) has become popular in contexts such as managing patient information and workflows. There are two broad categories of software that has been used to provide such systems:

Customized tailor made software (also known as "best-of-breed" software) which is custom developed for a particular implementation or situation. This is advantageous, in the sense that there is scope of case-specific tailoring. However, there are typically high development overheads, and challenges in integrating with other systems.

Enterprise software, which is implemented across a facility. This also comes with its advantages, particularly by reference to a broad range of functionalities that are often provided with relatively expansive software products, however there are inherent challenges in dealing with specific situations due to lack of customisation.

Furthermore, both approaches traditionally suffer from deficiencies in the sense that processes and procedures (and hence business requirements) develop and change over time, whilst software updates and modifications can be slow to keep up thereby to accommodate for such developments and changes.

SUMMARY OF THE INVENTION

It is an object of the present invention to overcome or ameliorate at least one of the disadvantages of the prior art, or to provide a useful alternative.

One embodiment provides a computer implemented method for providing Clinical Information System (CIS) functionalities, the framework including:

providing a plurality of purpose-specific CIS interfaces, wherein each interface is renderable at a given client terminal based on CIS interface design data, wherein the CIS interface design data includes:

(i) content pages, wherein each content page is configured to contain one or more page objects; and (ii) logical rules defining navigation and behaviour of content pages;

providing access to a common central patient information database, wherein the plurality of purpose specific CIS interfaces each have direct read and write access the common central patient information database;

providing access to a common Patient Administration System (PAS), wherein the plurality of purpose specific CIS interfaces each have direct native access to functionalities provided the common PAS;

providing a content and process design user interface, thereby to enable a user of a client terminal to define, by way of a graphical Interface, CIS interface design data; and operating a content and process engine configured to, based upon interaction between the client terminal and content and process design user interface, define content and process data for enabling rendering of a plurality of custom CIS user interfaces at distributed client terminals.

One embodiment provides a computer implemented framework for providing Clinical Information System (CIS) functionalities, the framework including:

a plurality of purpose-specific CIS interfaces, wherein each interface is renderable at a given client terminal based on CIS interface design data, wherein the CIS interface design data includes:

(i) content pages, wherein each content page is configured to contain one or more page objects; and (ii) logical rules defining navigation and behaviour of content pages; and a common central patient information database, wherein the plurality of purpose specific CIS interfaces each have direct read and write access the common central patient information database.

One embodiment provides a computer implemented framework for providing Clinical Information System (CIS) functionalities, the framework including:

a plurality of purpose-specific CIS interfaces, wherein each interface is renderable at a given client terminal based on CIS interface design data, wherein the CIS interface design data includes:

(i) content pages, wherein each content page is configured to contain one or more page objects; and (ii) logical rules defining navigation and behaviour of content pages; and a common Patient Administration System (PAS), wherein the plurality of purpose specific CIS interfaces each have direct native access to functionalities provided the common PAS.

One embodiment provides a computer implemented method for providing Clinical Information System (CIS) functionalities, the method including:

providing a content and process design user interface, thereby to enable a user of a client terminal to define, by way of a graphical Interface, CIS interface design data, wherein the CIS interface design data includes:

(i) content pages, wherein each content page is configured to contain one or more customisable page objects; and (ii) logical rules defining navigation and behaviour of content pages; and operating a content and process engine configured to, based upon interaction between the client terminal and content and process design user interface, define content and process data for enabling rendering of a plurality of custom CIS user interfaces at distributed client terminals.

One embodiment provides a computer implemented method for providing Clinical Information System (CIS) functionalities, the method including: enabling a user to generate CIS content data via a graphical content editing platform; and hosting the generated CIS content data thereby to allow a further user to interact with a CIS rendered based on the generated CIS data.

One embodiment provides a computer implemented method for providing Clinical Information System (CIS) functionalities, the method including:

providing a content and process design user interface, thereby to enable a user of a client terminal to graphically define CIS interface design data, wherein the CIS interface design data includes:

(i) content pages, wherein each content page is configured to contain one or more customisable page objects; and (ii) logical rules defining navigation and behaviour of content pages; and maintaining data indicative of a plurality of distinct CIS interfaces defined via the content and process design user interface;

enabling a user to customise a first customisable page object by:

(a) selecting a second customisable page object; and (b) setting a rule to use a value associated with a current user in respect of the second customisation page object.

One embodiment provides a computer implemented framework for providing Clinical Information System (CIS) functionalities, the framework including:

a plurality of purpose-specific CIS interfaces, wherein each interface is renderable at a given client terminal based on CIS interface design data, wherein the CIS interface design data includes:

(i) content pages, wherein each content page is configured to contain one or more page objects; and (ii) logical rules defining navigation and behaviour of content pages; and a monitoring engine configured to collect data representative of user interaction with each CIS interface, thereby to enable determination of process efficiency.

One embodiment provides a computer implemented method for providing Clinical Information System (CIS) functionalities, the method including:

providing a content and process design user interface, thereby to enable a user of a client terminal to define, by way of a graphical Interface, CIS interface design data, wherein the CIS interface design data includes:

(i) content pages, wherein each content page is configured to contain one or more customisable page objects; and (ii) logical rules defining navigation and behaviour of content pages; and wherein the user interface enables a given object to be associated with a formal value defined in an independent formal ontology.

One embodiment provides a computer program product for performing a method as described herein.

One embodiment provides a non-transitive carrier medium for carrying computer executable code that, when executed on a processor, causes the processor to perform a method as described herein.

One embodiment provides a system configured for performing a method as described herein.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Embodiments of the invention will now be described, by way of example only, with reference to the accompanying drawings in which.

DETAILED DESCRIPTION

Figure 1:
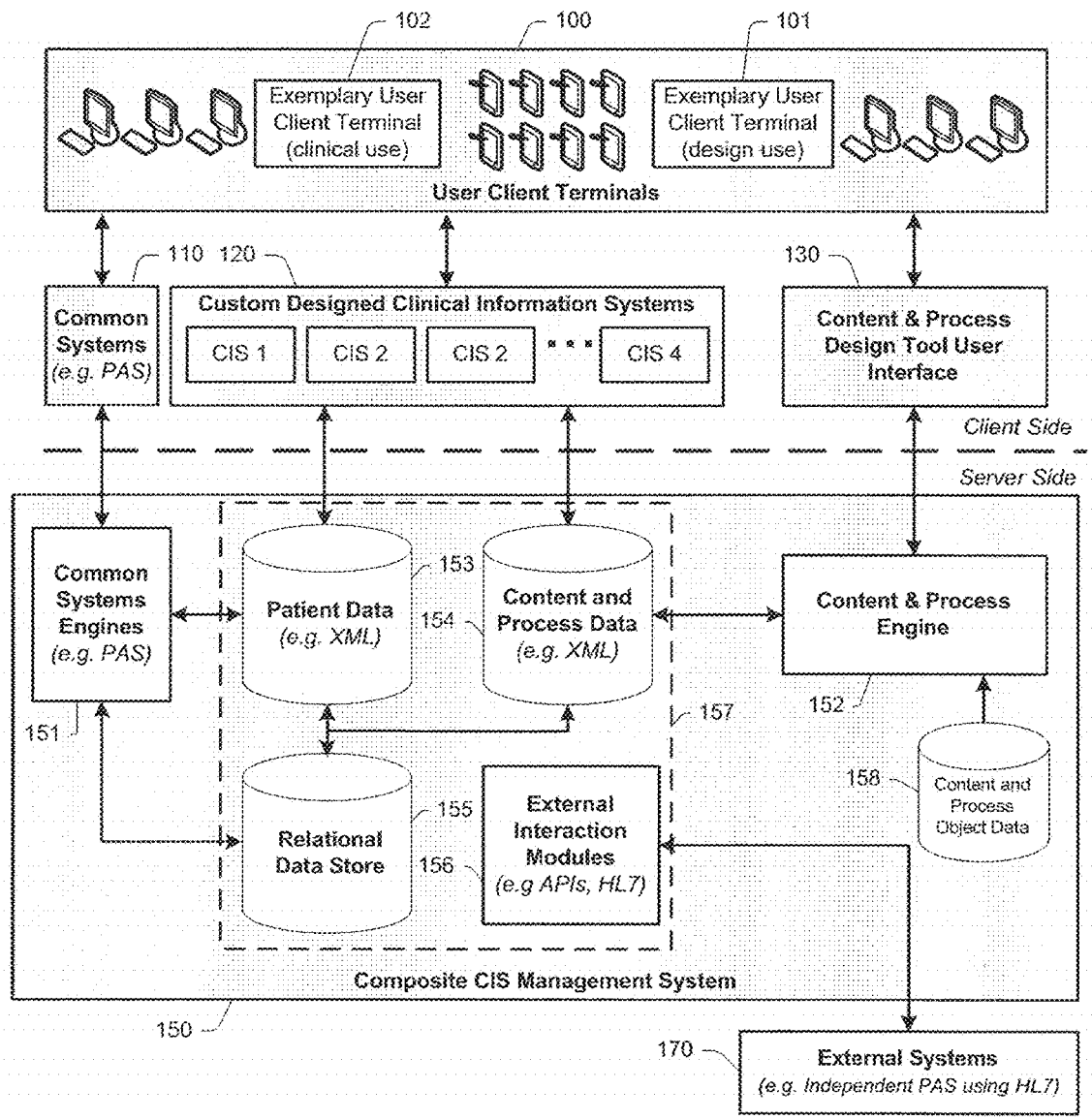
FIG. 1 schematically illustrates a framework according to one embodiment.

Described herein is technology including frameworks and methodologies configured to enable design and implementation of customised clinical information systems (CIS).

Some embodiments have been particularly developed for providing a hybrid between best-of-breed architecture and enterprise architecture, thereby to allow a clinical environment to leverage advantages associated with each. Some embodiments have been developed to enable native interoperability between customisable clinical information systems. Some embodiments have been developed to enable process efficiency management in clinical information systems. Some embodiments have been developed to enable implementation of independent formal ontology values in customised clinical information systems.

Various exemplary embodiments are discussed below.

General Overview

Embodiments described below relate to the provision of multiple Clinical Information System interfaces via a common framework. For example, a given healthcare facility may have individual CIS relating to the likes of oncology, emergency, radiology, colonoscopies, and so on.

The term "Clinical Information System" (referred to herein, in singular or plural, using the abbreviation CIS) describes a software-based product (i.e. a product that performs one or more computer executable methods via the execution of computer readable code using one or more processors) which provides functionality relevant to a clinical environment. This is used interchangeably with "CIS interface". The term "CIS user interface" describes a user interface rendered at a client terminal thereby to provide functional access to a given CIS. For example, a CIS user interface may be rendered in a web browser application, which downloads CIS interface design data from a server, or proprietary "parent" software application, which is able to load any one of multiple available CIS interfaces as functionally executable files.

The term "CIS interface design data" describes data indicative of CIS user interface components (such as pages and objects) and underlying logic, which is generated by a user, and enables the rendering of a CIS user interface.

A given CIS typically provides one or more "workflows". A workflow is a series of steps that are followed, for example involving data entry, thereby to assist in monitoring and/or management of clinical procedures and activities. For example, a workflow may be completed via the entry of information into a plurality of electronic forms. As described herein, these electronic forms are defined on "content pages". Each content page is configured to contain one or more page objects, such as:

Information objects (for example text-based data, such as a question or prompt, image data, video data, and so on).

Interactive buttons (for example a "submit" button, "next page" button, and so on).

Data fields, which are configured to contain values. These values may be user inputted, or automatically determined (for example as default values, calculated values, or values obtained from a specified source based on defined logic/rules).

It will be appreciated that this is a very basic selection of exemplary page objects only, and that a wide range of page objects may be present (for example using page objects known form general web page technology).

A workflow is additionally associated with logical rules defining navigation and behaviour of content pages. For example these define an order in which pages are completed (which may vary depending on observed values), allowable values for certain data fields, mandatory/optional statuses for certain data fields, and so on.

Various embodiments considered below provide a content and process design user interface, thereby to enable a user of a client terminal to graphically define CIS interface design data. For example, this content and process design user interface allows a user to create custom workflows. This is achieved by user-generation of content pages and logical rules. Preferably the content and process design user interface provides a selection of generic customisable page objects (for example buttons, data fields, and information objects). A user is enabled to place these onto a content page (for example using a "drag and drop" or other approach) and customise the objects by setting one or more parameters. Customisation may be achieved by providing access to, for a given object, a customisation menu which allows setting of parameters. This setting of parameters additionally allows for defining of logical rules. This provides a very user-friendly CIS generation tool, allowing for the creation and modification of workflows without any special software development and/or coding skills.

Each individual CIS leverages a common overall software infrastructure, for example leveraging a common set of patient management systems and databases. In this manner, general overarching CIS functionalities, which are required for all CIS systems (for example patient admission) are centralised and available to be shared. Accordingly, each individual CIS need only be concerned with its specific workflows that are relevant to the particular situation for it is designed. This provides advantages of "best-of-breed" software, in that each CIS is custom tailored for specific situations, (optionally be extremely specific in nature), whilst retaining overall infrastructural advantages typically associated with enterprise software.

Exemplary Framework

FIG. 1 illustrates a framework according to one embodiment. In overview, this framework provides CIS functionality to a plurality of client terminals 100, which may be substantially any form of computing devices (for example PCs, notebooks, tablets, smartphones, and so on). These client terminals may access CIS functionalities in two main ways:

Generation and/or modification of CIS interfaces (such as in the case of exemplary client terminal 101). As described further below, this is achieved by way of a content and process design tool user interface 130. User interface 130 may be provided, for instance, by way of a browser-based arrangement (user interface data is rendered via a web browser), or via a proprietary standalone software application.

Rendering of CIS user interfaces (such as in the case of exemplary client terminal 102), thereby to provide a user with access to workflows associated with a given CIS. This may be achieved by way of a browser-based arrangement (whereby CIS interface design data is rendered via a web browser thereby to provide a CIS user interface), a "parent" software approach (whereby CIS interface design data is rendered via a proprietary software application specially configured to load such data) or via multiple standalone software applications.

In relation to the latter, FIG. 1 illustrates common systems 110 (such as patient admission) and custom designed CIS interfaces 120 (for example discrete CIS interfaces for Emergency, Trauma, Colposcopy, Gynae Oncology, Breast Cancer, Multi-Disciplinary Meetings (MDM), Hysteroscopy, Surgical Wards, Oncology Wards, Theatre Management, Allied Health, Perioperative Services, Day Infusion, Ambulance, Colorectal Cancer, Haemo-Oncology, Lung Cancer, Neuro-Oncology, Sarcoma, Skin & Melanoma, Uro-Oncology, and so on).

Common systems 110 provide each of the custom designed CIS interfaces with native access to common functionalities, including the likes of PAS, analytics, and the like. That is, a suite of common functionalities required by a CIS are inherently natively available for each custom CIS 120 as a result of common systems 110.

Common systems 110, custom designed CIS interfaces 120, and user interface 130 are illustrated as client side components, in the sense that they provide functionality that is accessed by client devices 100. On the opposed server side there is provided a composite CIS management system 150, which may be defined by a single server, or by multiple (optionally distributed) server and/or other computing components.

System 150 provides back-end support to the various client side components. For example, common systems engines 151 provide server side functionality relating to patient management and the like, whilst content and process engine 152 provide service side functionality relevant to user interface 130. Code for enabling execution of custom CIS interfaces 120 is maintained in a content and process data repository 154 (also referred to as a CIS data repository, discussed in more detail further below).

A patient data repository 153 maintains data associated with each of a plurality of patients. This data includes details defined during patient registration (for example via a PAS included in common systems 151), and data defined by the operation of any one or more of CIS interfaces 120. That is, as a CIS interface is used, that may result in new data values being associated with a patient. Hosting all of this data in a common patient database is particularly valuable in the context of intra-CIS data sharing. Aspects of such data sharing are discussed in detail further below by reference to native interoperability.

Relational data store 155 is illustrated to graphically represent a single relational database that includes both patient data 153 and content/process data 154.

Data repositories 153-155 may be defined by any number of discrete database components, and are illustrated as three separate discrete database as an example only.

System 150 also provides external interaction modules 156, which enable interaction with external systems 170 (such as other software applications, databases, and the like). This may include interaction by way of APIs and/or by predefined interaction protocols, such as Health Level 7 (HL7) Standards or the like.

CIS Content Generation and Hosting

As shown in FIG. 1, content and process design user interface 130 operates in conjunction with a content and process engine 152. Engine 152 is configured to, based upon interaction between a given client terminal and user interface 130, define content and process data for enabling rendering of a custom CIS user interfaces at any of client terminals 100. More specifically, interaction with interface 130 causes engine 152 to generate CIS data, this CIS data being indicative of user-generated (or user-modified) content pages (and hence also logical rules defining navigation and behaviour of content pages, with those ruled being defined by customisation of page objects).

In the present embodiment, CIS data is maintained in a CIS data repository 154. In a preferred embodiment, this data is defined in XML format, for example defined in terms of page types, page objects, and page object parameters. CIS data (and hence CIS interfaces) are loaded from repository 154 and rendered as user interfaces on-demand. In this manner, each time a CIS interface is accessed by a client terminal 100 (or each time a given workflow is accessed), it is loaded from current CIS data. This allows modifications made to workflows to be made live substantially immediately.

Figure 2A:
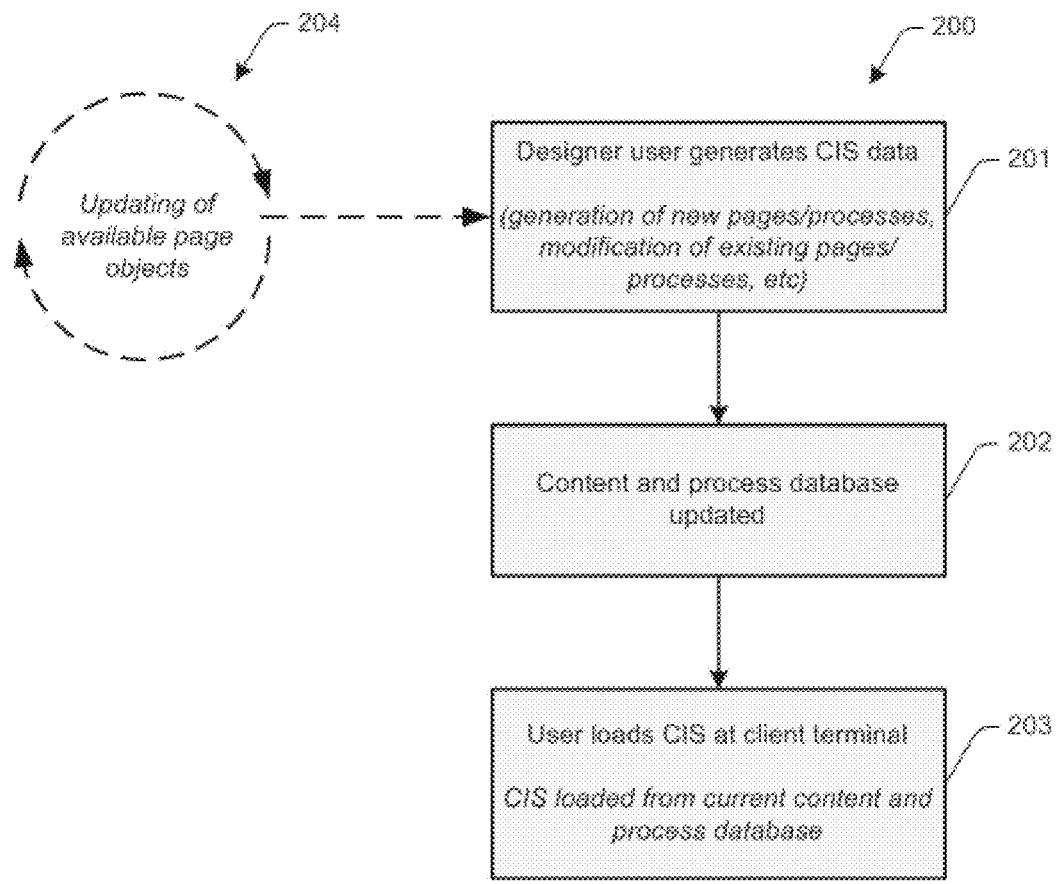
FIG. 2A and FIG. 2B illustrate methods according to various embodiments.

An overall process flow according to an embodiment is illustrated in method 200 of FIG. 2A. A user generates CIS data (which may include generating a new CIS/workflow/page, or modifying an existing CIS/workflow/page) at 201. Then, upon completion of 201, repository 154 is updated at 202. Then, at 203, a CIS interface is loaded (for example by downloading of code to enable rending of used interface components for one or more pages) by a client based on up-to-date CIS data from repository 154.

FIG. 2A also illustrates a looped process 204, which generally represents the updating of available page objects. As context, when a user selects a new page object for inclusion in a page, that is selected from a set of available customisable page objects (defined in repository 158). That set is updated on an ongoing basis, for example where a new form of page object requires development to solve a particular problem.

In relation to content generation, user interface 130 allows a user to either commence generation of an existing CIS interface, or modify an existing CIS interface (for example by modifying a particular workflow).

When a page (either new or existing) is opened in interface 130, a user is enabled to select an existing object, or add a new object of desired type (from the set of available customisable page objects). As noted, page objects may include the likes of Information objects (for example text-based data, such as a question or prompt, image data, video data, and so on).

Interactive buttons (for example a "submit" button, "next page" button, and so on).

Data fields, which are configured to contain values. These values may be user inputted, or automatically determined (for example as default values, calculated values, or values obtained from a specified source).

A user selects or adds an object at 211, and opens an object parameter setting interface (for example by double-clicking the object). The parameter setting interface provides a menu for allowing access to and setting of object parameters. These may include:

Visual parameters, such as font, colour, etc. Visual parameters such as size and position may in some cases be set graphically outside of the menu using drag/drop and stretch manipulations.

For information objects, the information that is to be displayed.

For interactive buttons, the function of the button (for example "submit", "next page", "previous page", and so on).

For data fields, the nature of data to be inputted (for example whether it is a date, time, value, etc), allowable value ranges, selectable values (for example if there is a drop-down menu), default values, pre-populated values, rules (for example whether a value is mandatory) and so on.

Semantic definitions of the fields using an established terminology, classification or ontology and a value set defining the range of values the field can be assigned. For example, these may allow the embedding of a standardised semantic definition in an object as a property of the object, for example using data drawn from a known published formal ontology (such as SNOMED CT). This allows objective categorisation of data based on independent standards.

Tables of data collated from information already stored about the patient.

FIG. 4A to FIG. 4D provide sample screenshots from an embodiment of user interface 130, showing various views relevant to customisation of page objects and the like.

In some cases logical rules may be defined for a data field, for example using IF, THEN, and ELSE logical operators. For example, in some cases a data field is set to be pre-populated with a value from patient database 153. If the data is not available, that may indicate that another workflow needs to be completed, and a rule is set to launch that workflow.

As foreshadowed above, in some embodiments the user interface enables a given object to be associated with a formal value defined in an independent formal ontology (such as SNOMED CT, or another ontology). Preferably, the user interface provides a search functionality thereby to assist a user in identifying the formal value based on one or more user generated object parameter values.

Native Interoperability

As noted, some cases, a data field is customized to be pre-populated with a value, for example a value from patient database 153. More broadly, various page objects may be configured to reference values in patient database 153 for a variety of reasons beyond display (for example to perform calculations, in the context of an "IF" operation, and so on).

Some embodiments implement a functionality referred to as native interoperability, which in essence allows for streamlined data sharing between CIS interfaces. In particular, this includes enabling a user to customise a first customisable page object by: (i) selecting a second customisable page object; and (ii) setting a rule to use a value associated with a current user in respect of the second customisation page object. For example, in a simple case this involves setting a data field to display a value that had previously been inputted via a data field in another CIS interface.

A key point is that the values are not defined by reference to specific database address codes. Rather, values are associated with the CIS interface, page, and page object from which they originate. In this manner, a user generating page content need not be familiar with database structure. They simply need to know in which workflow a value of current interest is inputted, and identify the page object via which it is inputted.

Figure 2B:
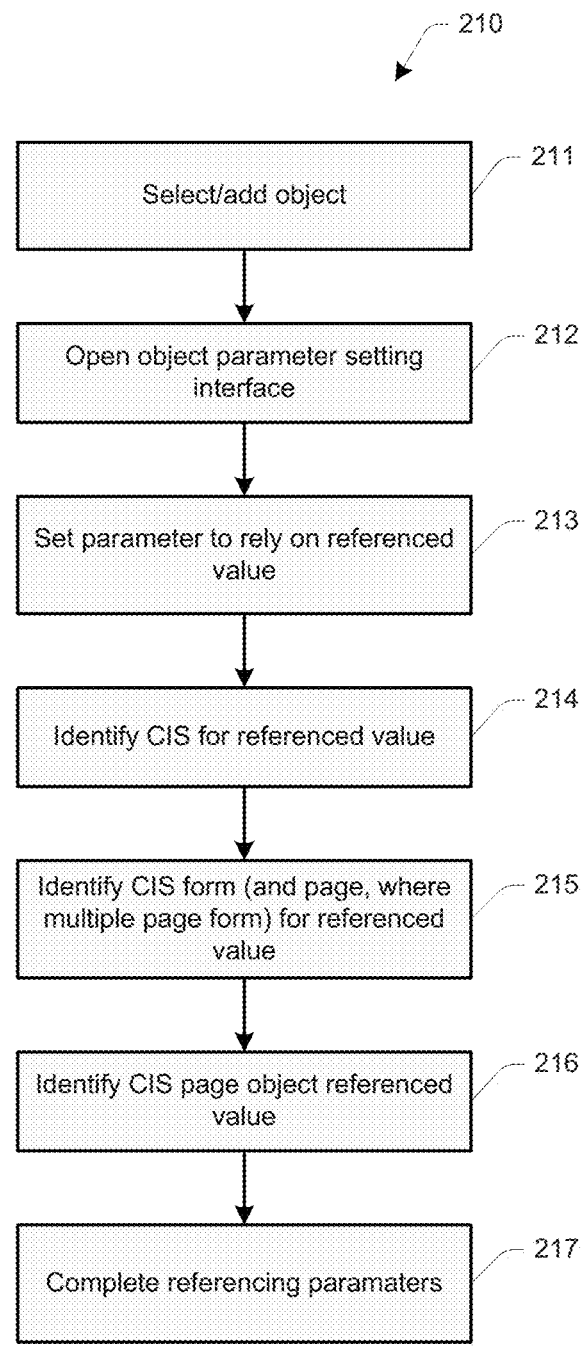

FIG. 2B illustrates an exemplary method 200 for utilising native interoperability. At 211 a user adds a new page object, or selects an existing page object. A parameter setting interface is opened at 212 (for example via a double click). At 213 a user makes a selection to rely on a referenced value, then identifies the relevant CIS (214), CIS form (and form page, where a given form spans multiple pages) (215) and page object (216). Referencing parameters are completed at 217.

CIS Content Sharing

In a similar vein to native interoperability, in some embodiments a user is enabled to insert pre-customised page objects that already exist on other pages (for example in other CIS interfaces). In this regard, repository 154 provides a library of customised content that may be leveraged in future content generation thereby to streamline procedures.

Process Efficiency

Some embodiments provide a methodology and mechanisms of Continuous Process Improvement (CPI). This is a critical aspect of work in busy departments. This includes providing "native analytics" on the data in the integrated architecture. This allows, for example:

(i) Analysis of work processes to identify the current costs (for example in the context of time overheads).

(ii) Immediate "on-the-spot" changeability to introduce a new work practice (for example based on an alteration to one or more CIS user interface pages, or one or more user interface components provided on a given CIS user interface page).

(iii) Analysis of the new work practices to determine if they did indeed introduce intended/anticipated improvements.

(iv) Ability to either continue with new practices, or alternately revert to old practices vie "on-the-spot" changeability.

In this manner, embodiments of the overall CIS technology described herein contain a mechanism for analysing the usability features of various defined operational workflows. This enables "native usability metrics and measurement"; at any time a given staff member is enabled to view and analyse how he/she uses (and/or other users use) a given CIS. For instance, in some cases this includes how often he/she moves (and/or how often other users move) in a path from screens A to B to C and the time spent on each screen). One user may spend four times longer flipping between one screen and another than others, but if piece of data were to be moved from one screen to another you would speed up the workflow. The described framework is configured to enable a rapid primary assessment, quickly and cheaply change a given CIS (e.g. a CIS page or rule), do the reassessment by looking up some automatically collected reporting tables and reinstate the old process immediately if needs be.

In this regard, one embodiment provides a computer implemented framework for providing Clinical Information System (CIS) functionalities, the framework including: a plurality of purpose-specific CIS interfaces, wherein each interface is renderable at a given client terminal based on CIS interface design data, wherein the CIS interface design data includes: (i) content pages, wherein each content page is configured to contain one or more page objects; and (ii) logical rules defining navigation and behaviour of content pages; and a monitoring engine configured to collect data representative of user interaction with each CIS interface, thereby to enable determination of process efficiency. The data representative of user interaction preferably includes data representing time taken for each of a plurality of users to complete a given workflow defined by one or more content pages. The framework is preferably configured to provide a comparison of data representing time taken to complete a given workflow, according to a first workflow configuration, with representing time taken to complete the same workflow according to a second workflow configuration.

Exemplary Client-Server Arrangement

Figure 3:
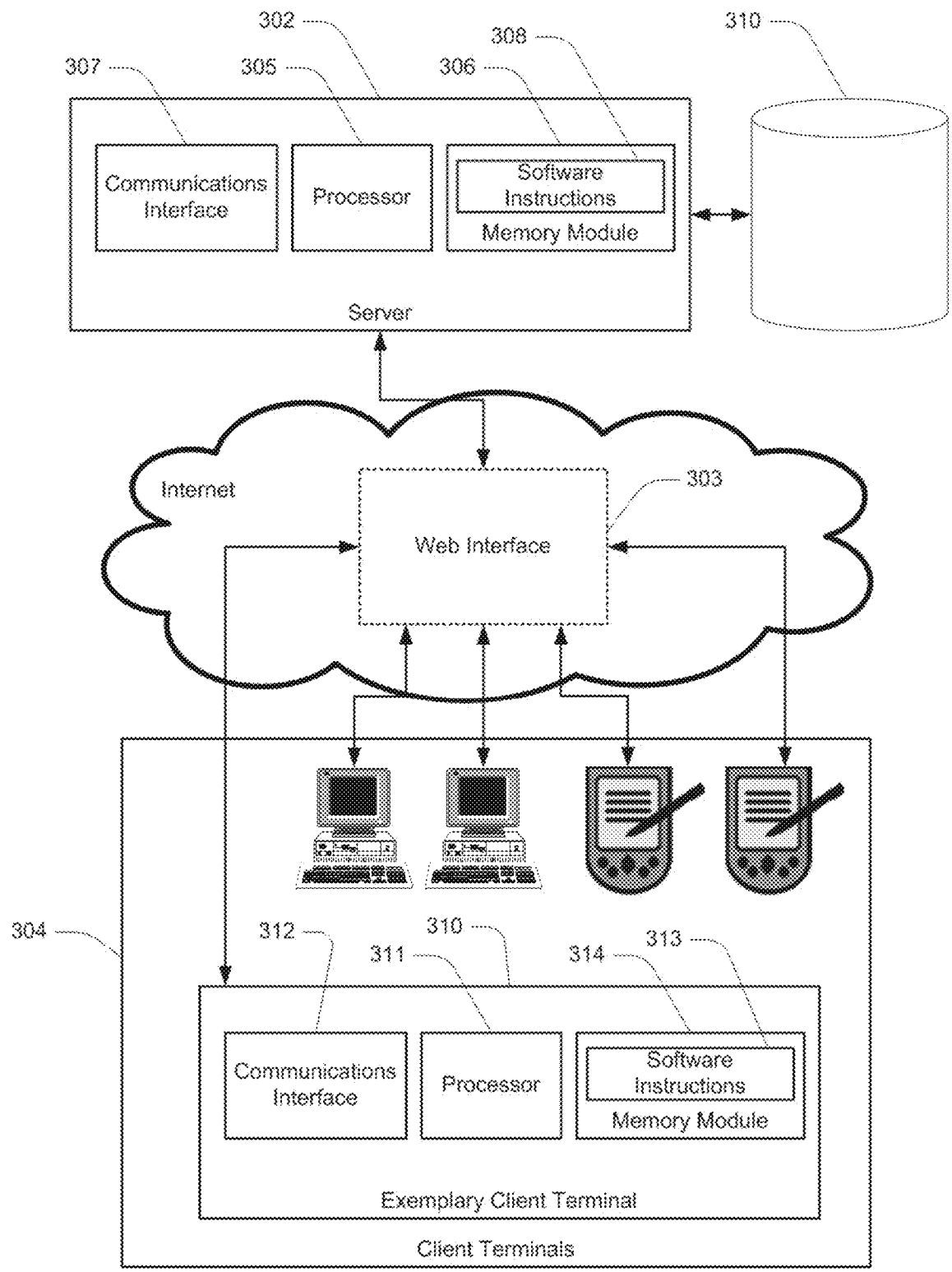
FIG. 3 illustrates an exemplary client-server framework.
Figure 4A:
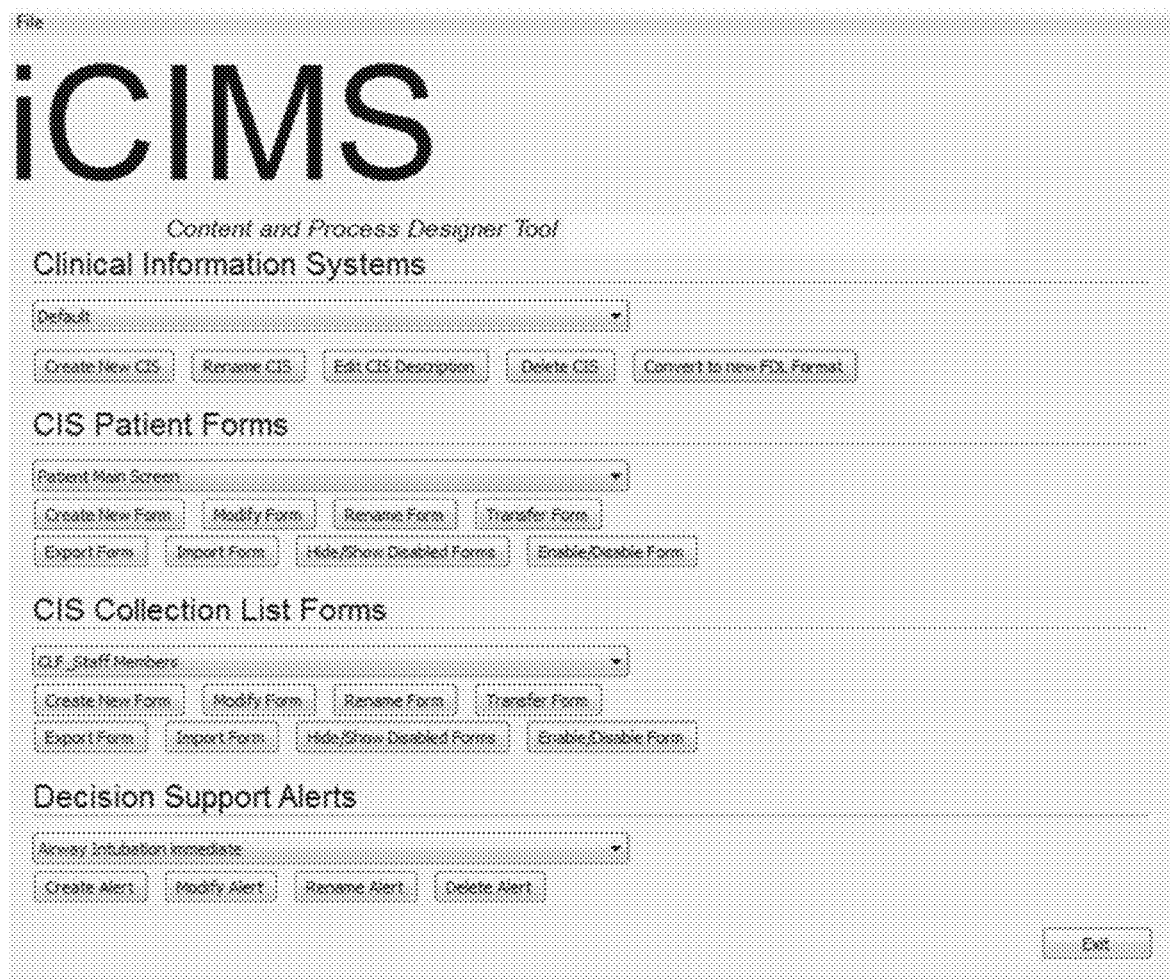
FIGS. 4A, 4B, 4C and 4D provide screenshots according to an exemplary embodiment.
Figure 4B:
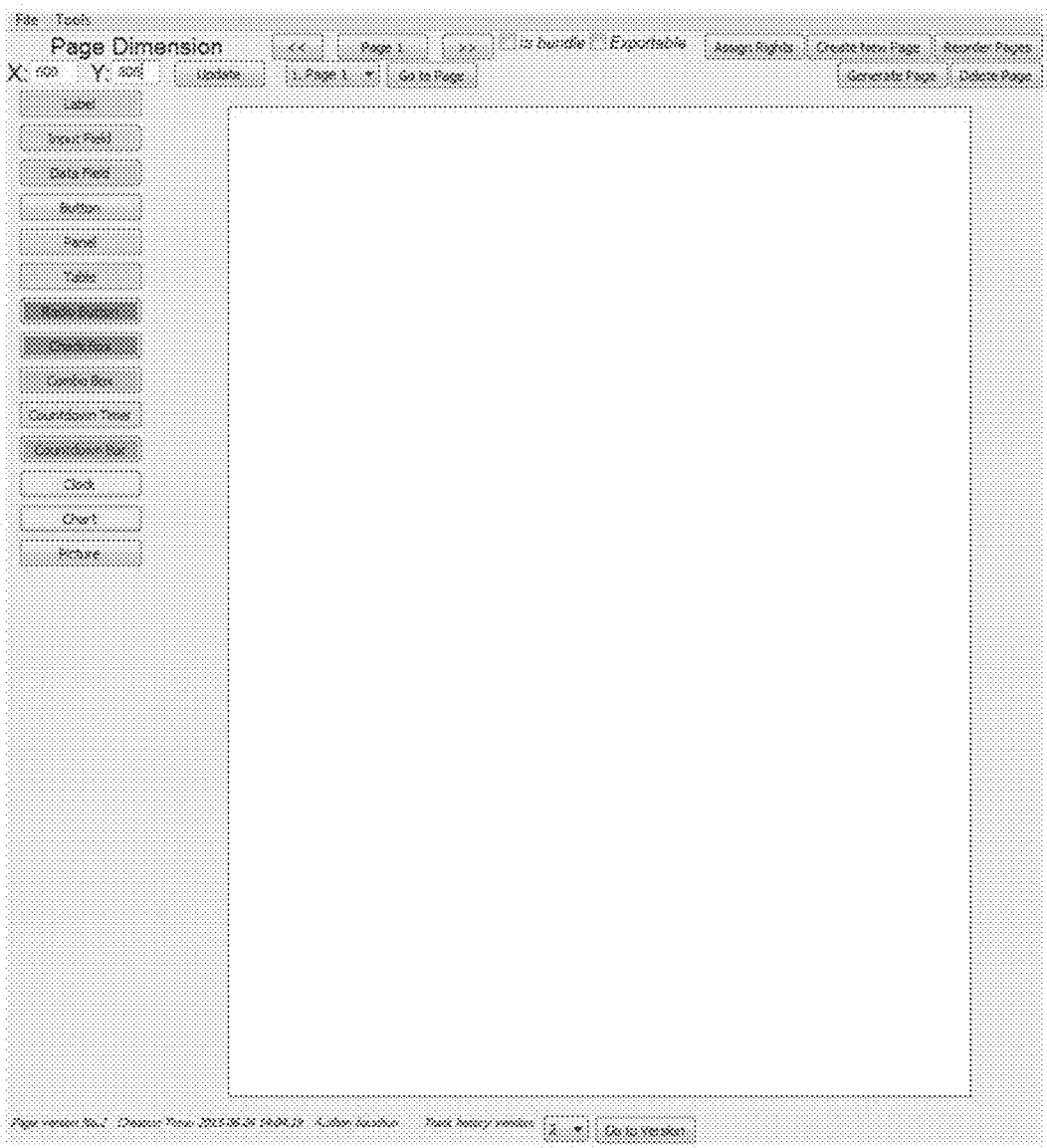
Figure 4C:
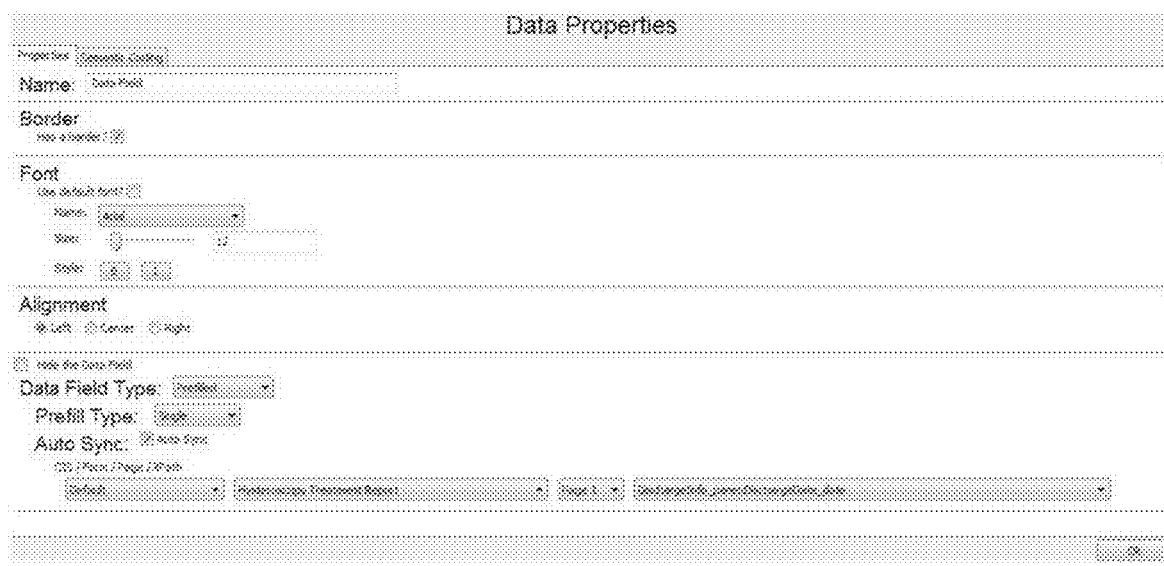
Figure 4D:
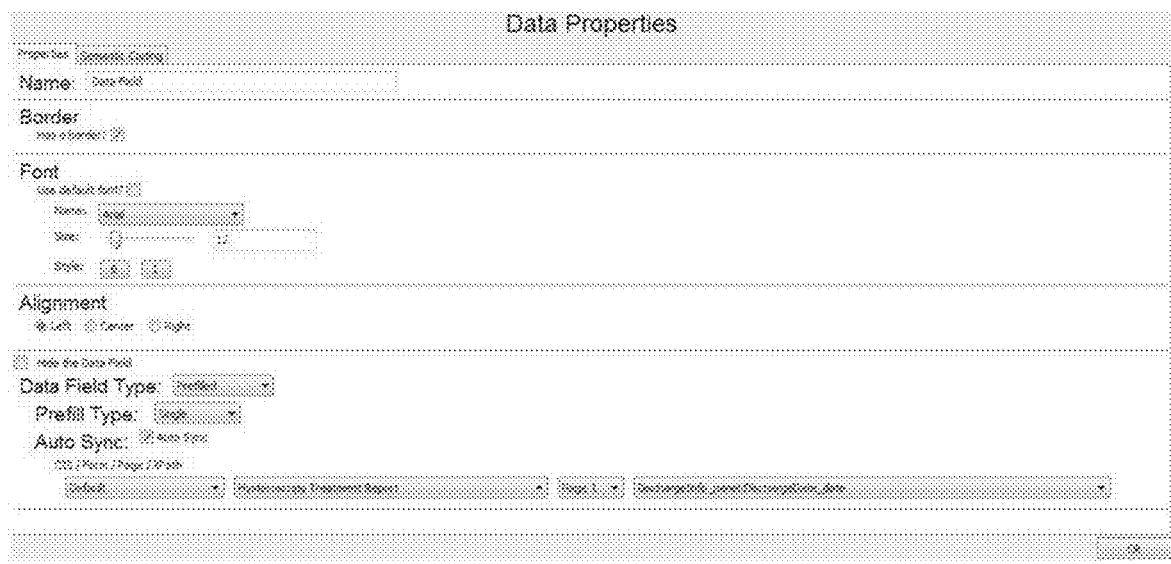

In some embodiments, methods and functionalities considered herein are implemented by way of a server, as illustrated in FIG. 3. In overview, a web server 302 provides a web interface 303. This web interface is accessed by the parties by way of client terminals 304. In overview, users access interface 303 over the Internet by way of client terminals 304, which in various embodiments include the likes of personal computers, PDAs, cellular telephones, gaming consoles, and other Internet enabled devices.

Server 303 includes a processor 305 coupled to a memory module 306 and a communications interface 307, such as an Internet connection, modem, Ethernet port, wireless network card, serial port, or the like. In other embodiments distributed resources are used. For example, in one embodiment server 302 includes a plurality of distributed servers having respective storage, processing and communications resources. Memory module 306 includes software instructions 308, which are executable on processor 305.

Server 302 is coupled to a database 310. In further embodiments the database leverages memory module 306.

In some embodiments web interface 303 includes a website. The term "website" should be read broadly to cover substantially any source of information accessible over the Internet or another communications network (such as WAN, LAN or WLAN) via a browser application running on a client terminal. In some embodiments, a website is a source of information made available by a server and accessible over the Internet by a web-browser application running on a client terminal. The web-browser application downloads code, such as HTML code, from the server. This code is executable through the web-browser on the client terminal for providing a graphical and often interactive representation of the website on the client terminal. By way of the web-browser application, a user of the client terminal is able to navigate between and throughout various web pages provided by the website, and access various functionalities that are provided.

Although some embodiments make use of a website/browser-based implementation, in other embodiments proprietary software methods are implemented as an alternative. For example, in such embodiments client terminals 304 maintain software instructions for a computer program product that essentially provides access to a portal via which framework 100 is accessed (for instance via an iPhone app or the like).

In general terms, each terminal 304 includes a processor 311 coupled to a memory module 313 and a communications interface 312, such as an internet connection, modem, Ethernet port, serial port, or the like. Memory module 313 includes software instructions 314, which are executable on processor 311. These software instructions allow terminal 304 to execute a software application, such as a proprietary application or web browser application and thereby render on-screen a user interface and allow communication with server 302. This user interface allows for the creation, viewing and administration of profiles, access to the internal communications interface, and various other functionalities.

Discussion of Advantages

Technology described herein provides for multiple individually designed CISs to run from the one server. Each CIS is designed by its own clinical team but installed to run on a joint server within the one version of the technology described herein. Each system has direct access to data in any other system where permission is provided, so that the records of the same patient being served by different clinical specialties can be directly accessed. Data fields in the one system can be set up to read from data input fields in another CIS. This approach removes the need for setting up message passing methods for exchanging data between the systems.

The effect is that each system can be developed independently yet the data they capture can be available to other CISs as and when it is needed without any other manual intervention.

This approach is particularly suited to research teams who need to build their own systems but also need a window into the records maintained by the clinical team. Instead of retrieving the paper record or visiting a distant site to view a record on a local computer the data is transported instantly to the research team the moment it is captured at the source point.

Technology described herein is based on knowledge that Clinical Information Systems are dynamic and need to evolve under the influence of a number of values, such as:

Evaluation and subsequent revision of work processes;
Changes in professional best practice;
New requirements introduced by professional judgement;
Introduction of research activities;
Movement of personnel.

An optimal methodology will facilitate the client's changes as a result of the above influences. It also acts to ensure that work practices are given their true value. This is achieved through evidence gleaned from the collection and analysis of appropriate data. Subsequently, the client's CIS should be changeable so that the appreciated value of newly devised work practices is implemented into the system as soon as they are defined. The CIS should then enable the new collection practices to be readily learnt and absorbed by the workforce. In this way, the CIS is both the Servant of Change and the Mechanism of Change without being the Director of Change whilst serving in the supply of value. It is through this evolutionary process that progress with successful IT will advance in a constructive and productive manner. It will be seen as positively constructive in creating valued change instead of the negative destructive wrecking of current good practices with the introduction of ill-suited IT.

A popular idea that by making clinical practices go digital will automatically bring process enhancements and efficiencies is one of the untenable assertions about e-Health.

Most current Health IT software electronically mechanises existing processes, but due to their inflexibility future evolution of the CIS is made more, not less, difficult.

Technology described herein, according to some embodiments, avoids the above traps in a number of ways:

Its approach to the analysis of the clinical processes allows for the current healthcare process to be absorbed into the designed system;
The systematic analysis of the current process that goes into producing a CIS as described herein forces clinicians, and data and business managers to reflect on current practice and encourages both innovative and evolutionary reform;

The adaptability of the technology described herein, which enables rapid changes to the design of systems, provides value in experimenting with different designs to optimise workable solutions;

The native interoperability within the technology described herein can save clinicians and associate scientists significant time in data entry, retrieval and review, as well as exporting better quality data to third parties involved in care and to external agencies; and, The inherent plasticity of technology described herein allows the IT to follow modifications in patient care and to facilitate an audit as well as clinical and translational research.

Technology described herein provides systems that are compact because they use the most advanced configurations of programming languages and multi-core processors. Modern technology allows for much more rapid transition to ever improving techniques in software engineering that better exploits the lower cost hardware that has come on to the market in the last 5 years. Larger and older ERP systems cannot move fast enough to exploit these technologies and therefore cannot bring down their costs nor deliver products that are so polished and well-tuned to clinicians needs.

Technology described herein can reproduce the client's current system and provide a number of other advantages to the current configuration, such as:

Data Validation—better validation of data as its input ensures more reliable data analytics.

Data Audit—technology described herein provides mechanisms for recording all activity of accessing screens and recording data, and so enables an audit of all user activity.

Data Extraction—technology described herein has a variety of tools for increasingly complex data extraction. At the simplest level, it has the capacity to extract any tabular information as CSV or XML files by using mechanisms for exporting forms. This comes as an intrinsic function without any need for programming.

Auto-coding of data according to SNOMED CT. Other coding schemes can be used where needed. This will create significant efficiencies for the medical record coding as required for statutory reporting.

Data Analytics—data analytics services will enable better analysis of the existing data. More complex levels of data analytics are available through the CliniDAL suite in the form of ad hoc questioning, hypothesis testing, concept based searching of text fields and predictive modelling.

The most advanced level is the development of predictive models to utilise the full value in any existing minimum dataset in order to identify the variables that best predict outcomes and then to apply them for prognostic purposes. This approach has been used previously for the Society of Plastic Surgeons on their breast implant database to identify the effectiveness of their minimum data set for predicting patient outcomes.

Automatic loading of data into a registry. technology described herein is able to be HL7-compliant, so any registry which can receive HL7 messages can be automatically loaded with the data from a compatible CIS.

Application Program Interfaces (APIs) are available to directly access system and patient data without needing to use messaging encoding and decoding processes. This mechanism is particularly useful for viewers that need to collect data from multiple system and then integrate the display of a unified patient record.

Conclusions and Interpretation

It will be appreciated that the disclosure above provides various significant frameworks and methodologies configured to enable design and implementation of customised clinical information systems Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Furthermore, a computer-readable carrier medium may form, or be included in a computer program product.

In alternative embodiments, the one or more processors operate as a standalone device or may be connected, e.g., networked to other processor(s), in a networked deployment, the one or more processors may operate in the capacity of a server or a user machine in server-user network environment, or as a peer machine in a peer-to-peer or distributed network environment. The one or more processors may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Note that while diagrams only show a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, one embodiment of each of the methods described herein is in the form of a computer-readable carrier medium carrying a set of instructions, e.g., a computer program that is for execution on one or more processors, e.g., one or more processors that are part of web server arrangement. Thus, as will be appreciated by those skilled in the art, embodiments of the present invention may be embodied as a method, an apparatus such as a special purpose apparatus, an apparatus such as a data processing system, or a computer-readable carrier medium, e.g., a computer program product. The computer-readable carrier medium carries computer readable code including a set of instructions that when executed on one or more processors cause the processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

The software may further be transmitted or received over a network via a network interface device. While the carrier medium is shown in an exemplary embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fiber optics, including the wires that comprise a bus subsystem. Transmission media also may also take the form of acoustic or light waves, such as those generated during radio wave and infrared data communications. For example, the term "carrier medium" shall accordingly be taken to included, but not be limited to, solid-state memories, a computer product embodied in optical and magnetic media; a medium bearing a propagated signal detectable by at least one processor of one or more processors and representing a set of instructions that, when executed, implement a method; and a transmission medium in a network bearing a propagated signal detectable by at least one processor of the one or more processors and representing the set of instructions.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

It should be appreciated that in the above description of exemplary embodiments of the invention, various features of the invention are sometimes grouped together in a single embodiment, FIG. or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A computer implemented method for providing Clinical Information System (CIS) functionalities, comprising:
    providing a plurality of purpose-specific CIS interfaces, wherein each interface is renderable at a given client terminal based on CIS interface design data, wherein the CIS interface design data includes:
        (i) content pages, wherein each content page is configured to contain one or more page objects; and
        (ii) logical rules defining navigation and behaviour of the content pages;
    wherein each of the plurality of purpose-specific CIS interfaces is configured to retrieve and input patient information to a common central patient information database;
    wherein each of the plurality of purpose-specific CIS interfaces has direct native access to functionalities of a common Patient Administration System (PAS);
    displaying, via the client terminal, a plurality of page objects;
    receiving, via a graphical interface, a selection of a page object of the plurality of page objects;
    in response to receiving the selection of the page object, opening an object parameter setting interface of the page object;
    receiving, via the graphical interface, a selection of an object parameter;
    associating the selected object parameter with a pre-defined formal value;
    identifying, via a processor, a purpose-specific CIS interface of the plurality of purpose-specific CIS interfaces associated with the formal value; and
    in response to receiving the formal value, generating via a processor a custom CIS user interface.

2. The framework according to claim 1, wherein the plurality of page objects is expandable by administrator definition of one or more new or modified customisable objects.

3. The framework according to claim 1, wherein the one or more page objects are customisable page objects, and wherein the page objects include: information objects, interactive buttons, input fields, and data fields.

4. The method according to claim 1, wherein the pre-defined formal value is defined in an independent formal ontology.

5. The method according to claim 1, wherein the page objects include at least one of a data object and/or a process object.

6. A system for delivering a computer implemented framework for providing Clinical Information System (CIS) functionalities, the framework including:
    a plurality of purpose-specific CIS interfaces, wherein each interface is renderable at a given client terminal based on CIS interface design language, wherein the CIS interface design language includes:
        (i) content pages, wherein each content page is configured to contain one or more page objects; and
        (ii) logical rules defining navigation and behaviour of the content pages; and
    a common central patient information database, wherein the plurality of purpose specific CIS interfaces each have direct read and write access of the common central patient information database, wherein the system comprises:
        a CIS management system on one or more servers comprising:
            a content and process design user interface configured with instructions stored in a non-transitory memory to define content and process data for enabling creation of the plurality of purpose-specific CIS interfaces;
            a content and process data repository configured with instructions stored in the non-transitory memory for rendering the plurality of purpose-specific CIS interfaces; and
            a content and process engine configured with instructions stored in the non-transitory memory to generate CIS data, the CIS data being indicative of user-generated content pages and comprising the logical rules defining navigation and behaviour of the content pages, wherein the user-generated content pages are based on a user selection of page objects configured to reference values in a patient data repository; and
        an external interaction module communicatively coupled to the CIS management system and configured to enable interaction of the CIS management system with external applications.

7. The framework according to claim 6, including the content and process design user interface that provides design users with a graphical editor interface thereby to define and/or modify one or more of the plurality of purpose-specific CIS interfaces.

8. The framework according to claim 7, wherein the content and process design user interface enables a design user to select a customisation page object from a set of available objects, and customise that object by setting one or more parameters.

9. The framework according to claim 8, wherein the set of available objects is expandable by administrator definition of one or more new or modified customisable objects.

10. The framework according to claim 6, wherein the one or more page objects are customisable page objects defined and/or modified via the content and process design user interface, wherein the page objects include: information objects, interactive buttons, input fields, and data fields.

11. A computer implemented method for providing Clinical Information System (CIS) functionalities, the method including:
    providing a content and process design user interface, thereby to enable a design user to define, by way of a graphical Interface, CIS interface design data, wherein the CIS interface design data includes content pages, wherein each content page is configured to contain one or more customisable page objects;
    displaying, via a client terminal, a content page comprising the one or more customisable page objects;

receiving, via a graphical interface, a selection of a page object of the one or more customisable page objects;

in response to receiving the selection of the page object, opening an object parameter setting interface of the page object;

receiving, via a graphical interface, a selection of an object parameter;

associating the selected object parameter with a pre-defined formal value;

identifying a CIS interface of a plurality of CIS interfaces associated with the pre-defined formal value; and in response to receiving the pre-defined formal value, generating a custom CIS user interface at distributed clinician client terminals, wherein each custom CIS user interface has direct read and write access to a common set of patient management systems and databases.

12. The method according to claim 11, wherein a set of available page objects is expandable by administrator definition of one or more new or modified customisable page objects.

13. The method according to claim 11, wherein the one or more customisable page objects include: information objects, interactive buttons, input fields, and data fields.

14. The method according to claim 11, wherein the common set of patient management systems and databases includes a common patient registration and management system.

15. The method according to claim 11 wherein defining, by way of the graphical interface, includes customising a given page object to obtain a data value inputted by a specified further page object.

16. The method according to claim 15, wherein the specified further page object is defined on a page other than the content page currently being edited.

17. The method according to claim 15, wherein the specified further page object is defined on a page belonging to a CIS system other than the CIS system which contains the content page currently being edited.

18. The method according to claim 11, wherein the common set of patient management systems and databases includes a common patient database.

* * * * *